US011685888B2

(12) United States Patent
Nakai et al.

(10) Patent No.: US 11,685,888 B2
(45) Date of Patent: Jun. 27, 2023

(54) METHOD FOR PRODUCING PRODUCT

(71) Applicant: FUJIFILM Corporation, Tokyo (JP)

(72) Inventors: Shinichi Nakai, Kanagawa (JP); Naoto Takahashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 538 days.

(21) Appl. No.: 16/807,740

(22) Filed: Mar. 3, 2020

(65) Prior Publication Data

US 2020/0216792 A1 Jul. 9, 2020

Related U.S. Application Data

(63) Continuation of application No. PCT/JP2018/032678, filed on Sep. 3, 2018.

(30) Foreign Application Priority Data

Sep. 6, 2017 (JP) ................................ 2017-171331
Nov. 10, 2017 (JP) ................................ 2017-217395

(51) Int. Cl.
C12M 1/42 (2006.01)
C12M 1/00 (2006.01)
C12M 1/26 (2006.01)
C12M 1/36 (2006.01)

(52) U.S. Cl.
CPC ............ *C12M 35/04* (2013.01); *C12M 23/34* (2013.01); *C12M 33/14* (2013.01); *C12M 41/48* (2013.01)

(58) Field of Classification Search
None
See application file for complete search history.

(56) References Cited

U.S. PATENT DOCUMENTS

| 2010/0167396 | A1* | 7/2010 | Murphy ................ A61K 38/17 435/375 |
| 2013/0109086 | A1 | 5/2013 | Kobayashi et al. |
| 2014/0011270 | A1 | 1/2014 | Chotteau et al. |
| 2014/0087424 | A1 | 3/2014 | Crowley et al. |
| 2014/0093952 | A1 | 4/2014 | Serway |

FOREIGN PATENT DOCUMENTS

| CN | 102971411 A | 3/2013 |
| CN | 104388324 A | 3/2015 |
| JP | 2014-207959 A | 4/2014 |
| WO | WO 2016/100923 A1 | 6/2016 |

OTHER PUBLICATIONS

Wang et al. Journal of Biotechnology, 2017, 246, pp. 52-60.*
Durmus et al., Magnetic levitation of single cells,* PNAS, vol. 112, No. 28, Jun. 29, 2015, XP055581767, pp. 1-8.
Extended European Search Report, dated Jul. 2, 2020, for European Application No. 18853414.3.
Gorenflo et al., "Scale-Up and Optimization of an Acoustic Filter for 200 L/day Perfusion of a CHO Cell Culture," Biotechnology and Bioengineering, vol. 80, No. 4, Sep. 24, 2002, XP055440282, pp. 438-444.
Iding et al., "Influence of alterations in culture condition and changes in perfusion parameters on the retention performance of a 20 μm spinfilter during a perfusion cultivation of a recombinant CHO cell line in pilot scale," Cytotechnology, vol. 34, Jan. 1, 2020, XP055705687, pp. 141-150.
Karst et al., "Characterization and comparison of ATF and TFF in stirred bioreactors for continuous mammalian cell culture processes," Biochemical Engineering Journal, Elsevier, vol. 110, Feb. 8, 2016, XP029470797, pp. 17-26.
Zhang et al., "Very high cell densify perfusion of CHO cells anchored in a non-woven matrix-based bioreactor," Journal of Biotechnology, Elsevier, vol. 213, Jul. 23, 2015, XP029284039, pp. 28-41.
Author Unknown, "Compressed Mode Aspects of DCH Enhancements," 3GPP TSG RAN WG1 Meeting #76bis, R1-141702, Shenzhen, China, Mar. 31-Apr. 4, 2014, 7 pages total.
Clincke et al., "Very High Density of Chinese Hamster Ovary Cells in Perfusion by Alternating Tangential Flow or Tangential Flow Filtration in WAVE Bioreactor™—Part II: Applications for Antibody Production and Cryopreservation," Biotechnology Progress, vol. 29, No. 3, 2013, 11 pages total.
Japanese Notice of Reasons for Refusal for corresponding Japanese Application No. 2019-540952, dated Oct. 6, 2020, with an English translation.
Clinke et al., "Very High Density of Chinese Hamster Ovary Cells in Perfusion by Alternating Tangential Flow or Tangential Flow Filtration in WAVE Bioreactor™—Part II: Applications for Antibody Production and Cryopreservation", Blotechnol. Prog., 2013, vol. 29, No. 3, pp. 768-777 ( 10 pages).
International Preliminary Report on Patentability and Written Opinion of the International Searching Authority(Forms PCT/IB/326, PCT/IB/373 and PCT/ISA/237), dated Mar. 19, 2020, for International Application No. PCT/JP2018/032678, with an English Translation.
International Search Report (Form PCT/ISA/210) dated Nov. 13, 2018, for International Application No. PCT/JP2018/032678, with an English translation.
Karst et al., "Characterization and comparison of ATF and TFF in stirred bioreactors for continuous mammalian cell culture processes (Electronic Supplementary Information)", Biochemical Engineering Journal, pp. 1-20 (20 pages).

(Continued)

*Primary Examiner* — Vera Afremova

(74) *Attorney, Agent, or Firm* — Birch, Stewart, Kolasch & Birch, LLP

(57) ABSTRACT

A method for producing a product related to the specified technology includes adjusting the concentration of cells in a culture vessel to a value of from $3\times10^7$ cells/ml to $3\times10^8$ cells/ml; in a case in which the average diameter of single cells in the culture vessel is designated as A, adjusting the number proportion of cells having a single cell diameter of 1.4×A or greater in the culture vessel to 5% or less, and adjusting the number proportion of cells having a single cell diameter in the range of A±A/7 to 50% or more.

11 Claims, 3 Drawing Sheets

(56) References Cited

OTHER PUBLICATIONS

Wang et al., "Shear contributions to cell culture performance and product recovery in ATF and TFF perfusion systems", Journal of Biotechnology, Jan. 2017, vol. 246, pp. 52-60 (16 pages).
Chinese Office Action and Search Report for corresponding Chinese Application No. 201880056019.4, dated Feb. 13, 2023, with English translation.

* cited by examiner

FIG. 3

| EXAMPLE | TYPE OF CELL | CELL CONCENTRATION ×10⁷ [cells/mL] | AVERAGE VALUE OF CELL DIAMETER A [μm] | STANDARD DEVIATION OF CELL DIAMETER σ [μm] | NUMBER PROPORTION OF CELLS HAVING DIAMETER OF 1.4A OR LARGER [%] | NUMBER PROPORTION OF CELLS HAVING DIAMETER OF A ± A/7 [%] | TYPE OF PUMP | SEPARATION METHOD | TYPE OF FILTER | FILTRATION METHOD | DIAMETER OF ROTATING BLADE D [m] | DISTANCE FROM BLADE TO INNER WALL L [m] | ROTATION SPEED OF PUMP R [rpm] | VISCOSITY OF CELL SUSPENSION X [Pa·s] | SHEAR STRESS Y [Pa] | LIQUID FEEDING PRESSURE P [Pa] | INDEX VALUE F = Y×10000+P [Pa] | log₁₀(P/Y) | SURVIVAL RATE OF CELLS [%] | DETERMINATION | PROPORTION OF MAIN PEAK (ANTIBODY QUALITY) DETERMINATION |
|---|---|---|---|---|---|---|---|---|---|---|---|---|---|---|---|---|---|---|---|---|---|
| EXAMPLE 1 | CHO CELL | 8.5 | 13.2 | 2.3 | 2.2 | 69 | MAGNETIC LEVITATION TYPE PUMP [1] | SEPARATION MEMBRANE | HOLLOW FIBER TYPE MF MEMBRANE | TFF | 0.042 | 0.005 | 2000 | 0.0019 | 1.670 | 10300 | 27006 | 3.790 | 97.6 | A | A |
| EXAMPLE 2 | CHO CELL | 8.5 | 13.4 | 2.4 | 2.4 | 70 | MAGNETIC LEVITATION TYPE PUMP [2] | SEPARATION MEMBRANE | HOLLOW FIBER TYPE MF MEMBRANE | TFF | 0.035 | 0.0085 | 2000 | 0.0019 | 0.819 | 8300 | 16489 | 4.006 | 97.4 | A | A |
| EXAMPLE 3 | CHO CELL | 8.5 | 13.4 | 2.4 | 2.4 | 68 | MAGNETIC LEVITATION TYPE PUMP [3] | SEPARATION MEMBRANE | HOLLOW FIBER TYPE MF MEMBRANE | TFF | 0.019 | 0.005 | 2000 | 0.0019 | 0.756 | 5300 | 12857 | 3.846 | 97.4 | A | A |
| EXAMPLE 4 | CHO CELL | 8.5 | 13.1 | 2.3 | 2.1 | 66 | MAGNETIC LEVITATION TYPE PUMP [4] | SEPARATION MEMBRANE | HOLLOW FIBER TYPE MF MEMBRANE | TFF | 0.05 | 0.0175 | 2000 | 0.0019 | 0.568 | 16800 | 22482 | 4.471 | 97.6 | A | A |
| EXAMPLE 5 | CHO CELL | 8.5 | 13 | 2.3 | 2 | 67 | MAGNETIC LEVITATION TYPE PUMP [5] | SEPARATION MEMBRANE | HOLLOW FIBER TYPE MF MEMBRANE | TFF | 0.07 | 0.0505 | 2000 | 0.0019 | 0.276 | 19100 | 21857 | 4.841 | 97.6 | A | A |
| EXAMPLE 6 | CHO CELL | 8.5 | 13.6 | 2.7 | 2.9 | 58 | MAGNETIC LEVITATION TYPE PUMP [2] | SEPARATION MEMBRANE | HOLLOW FIBER TYPE MF MEMBRANE | TFF | 0.035 | 0.0085 | 600 | 0.0019 | 0.246 | 8400 | 10857 | 4.534 | 95.4 | B | B |
| EXAMPLE 7 | CHO CELL | 8.5 | 13.6 | 2.7 | 3.3 | 56 | MAGNETIC LEVITATION TYPE PUMP [2] | SEPARATION MEMBRANE | HOLLOW FIBER TYPE MF MEMBRANE | TFF | 0.035 | 0.0085 | 300 | 0.0019 | 0.123 | 7400 | 8628 | 4.780 | 93.9 | B | B |
| EXAMPLE 8 | CHO CELL | 8.5 | 12.9 | 2.8 | 2.6 | 58 | MAGNETIC LEVITATION TYPE PUMP [2] | SEPARATION MEMBRANE | HOLLOW FIBER TYPE MF MEMBRANE | TFF | 0.042 | 0.005 | 2800 | 0.0019 | 2.339 | 12400 | 35787 | 3.724 | 93.1 | C | C |
| EXAMPLE 9 | CHO CELL | 8.5 | 12.7 | 2.7 | 3.1 | 57 | MAGNETIC LEVITATION TYPE PUMP [1] | SEPARATION MEMBRANE | HOLLOW FIBER TYPE MF MEMBRANE | TFF | 0.042 | 0.005 | 3300 | 0.0019 | 2.756 | 16000 | 43563 | 3.764 | 91.3 | C | C |
| EXAMPLE 10 | CHO CELL | 8.5 | 12.6 | 3.2 | 3.4 | 54 | MAGNETIC LEVITATION TYPE PUMP [1] | SEPARATION MEMBRANE | HOLLOW FIBER TYPE MF MEMBRANE | TFF | 0.042 | 0.005 | 3300 | 0.0019 | 2.756 | 47000 | 74563 | 4.232 | 90.3 | C | C |
| EXAMPLE 11 | CHO CELL | 8.5 | 13.6 | 2.8 | 4.1 | 52 | MAGNETIC LEVITATION TYPE PUMP [2] | SEPARATION MEMBRANE | HOLLOW FIBER TYPE MF MEMBRANE | TFF | 0.035 | 0.0085 | 300 | 0.0019 | 0.123 | 47000 | 48228 | 5.583 | 91.4 | C | C |
| EXAMPLE 12 | CHO CELL | 8.5 | 12.6 | 3.2 | 3.5 | 51 | MAGNETIC LEVITATION TYPE PUMP [1] | SEPARATION MEMBRANE | HOLLOW FIBER TYPE MF MEMBRANE | TFF | 0.042 | 0.005 | 3300 | 0.0019 | 2.756 | 6200 | 33763 | 3.352 | 91.2 | C | C |
| EXAMPLE 13 | CHO CELL | 8.5 | 12.7 | 2.6 | 2.6 | 63 | MAGNETIC LEVITATION TYPE PUMP [1] | SOUND WAVE SEPARATION | SOUND WAVE SEPARATION | SOUND WAVE SEPARATION | 0.042 | 0.005 | 2300 | 0.0019 | 1.921 | 11400 | 30611 | 3.773 | 96.2 | B | B |
| EXAMPLE 14 | CHO CELL | 5.4 | 13.2 | 2.4 | 2.1 | 67 | MAGNETIC LEVITATION TYPE PUMP [1] | SEPARATION MEMBRANE | HOLLOW FIBER TYPE MF MEMBRANE | TFF | 0.042 | 0.005 | 2000 | 0.0016 | 1.407 | 9800 | 23867 | 3.843 | 97.8 | A | A |
| EXAMPLE 15 | CHO CELL | 3.4 | 13.2 | 2.4 | 2 | 66 | MAGNETIC LEVITATION TYPE PUMP [1] | SEPARATION MEMBRANE | HOLLOW FIBER TYPE MF MEMBRANE | TFF | 0.042 | 0.005 | 2000 | 0.0013 | 1.143 | 9600 | 21030 | 3.924 | 98.1 | A | A |
| COMPARATIVE EXAMPLE 1 | CHO CELL | 8.5 | 14 | 3.6 | 5.2 | 48 | DIAPHRAGM TYPE RECIPROCATING PUMP ATF | SEPARATION MEMBRANE | HOLLOW FIBER TYPE MF MEMBRANE | ATF | - | - | - | - | - | - | - | - | 91 | D | D |
| COMPARATIVE EXAMPLE 2 | CHO CELL | 8.5 | 13.8 | 3.6 | 5.5 | 46 | MAGNETIC LEVITATION TYPE PUMP [2] | SEPARATION MEMBRANE | HOLLOW FIBER TYPE MF MEMBRANE | TFF | 0.035 | 0.0085 | 200 | 0.0019 | 0.082 | 400 | 1219 | 3.689 | 90.7 | D | D |
| COMPARATIVE EXAMPLE 3 | CHO CELL | 8.5 | 11.9 | 3.1 | 3.8 | 47 | MAGNETIC LEVITATION TYPE PUMP [1] | SEPARATION MEMBRANE | HOLLOW FIBER TYPE MF MEMBRANE | TFF | 0.042 | 0.005 | 3800 | 0.0019 | 3.174 | 52000 | 83739 | 4.214 | 87.5 | E | D |
| COMPARATIVE EXAMPLE 4 | CHO CELL | 8.5 | 13 | 3.4 | 4.1 | 46 | MAGNETIC LEVITATION TYPE PUMP [2] | SEPARATION MEMBRANE | HOLLOW FIBER TYPE MF MEMBRANE | TFF | 0.035 | 0.0085 | 300 | 0.0019 | 0.123 | 70000 | 71228 | 5.756 | 90.6 | D | D |
| COMPARATIVE EXAMPLE 5 | CHO CELL | 8.5 | 12 | 3.1 | 4.4 | 45 | MAGNETIC LEVITATION TYPE PUMP [1] | SEPARATION MEMBRANE | HOLLOW FIBER TYPE MF MEMBRANE | TFF | 0.042 | 0.005 | 3800 | 0.0019 | 3.174 | 2700 | 34439 | 2.930 | 88.7 | E | D |

METHOD FOR PRODUCING PRODUCT

CROSS-REFERENCE TO RELATED APPLICATION

This application is a continuation application of International Application No. PCT/JP2018/032678, filed Sep. 3, 2018, the disclosure of which is incorporated herein by reference in its entirety. Further, this application claims priority from Japanese Patent Application No. 2017-171331 filed on Sep. 6, 2017, and Japanese Patent Application No. 2017-217395 filed on Nov. 10, 2017, the disclosures of which are incorporated herein by reference in its entirety.

BACKGROUND

1. Technical Field

The disclosed technology relates to a method for producing a product produced from cells.

2. Description of the Related Art

With regard to the production of biomedicines and the like that include antibodies produced from cells, perfusion culture is known, in which a medium including antibodies is continuously extracted from a culture vessel while a fresh medium is continuously supplied to the culture vessel in order to increase the productivity of antibodies.

Regarding a technology related to perfusion culture, for example, it is described in JP2014-507959A that insufficient cell growth is observed in connection with the occurrence that the average cell diameter increases.

Furthermore, in Characterization and comparison of ATF and TFF in stirred bioreactors for continuous mammalian cell culture processes (Biochemical Engineering Journal 110 (2016) 17-26), it is described that in a culture carried out using a magnetic levitation type pump, culture results equivalent to the results obtainable with an ATF (Alternating Tangential Flow Filtration) diaphragm type reciprocating pump are obtained.

SUMMARY

When perfusion culture is performed, high cell concentration culture is enabled, and the productivity of products such as antibodies produced from cells is increased. However, in a case in which the cell concentration in the culture vessel increases, there is a problem that the viability of cells may decrease, or the product quality of the products produced from cells may decrease.

According to an embodiment of the invention, the product quality of a product is increased while the productivity of the product based on high cell concentration culture is maintained.

A method for producing a product according to the disclosed technology is a method for producing a product that is produced from cells accommodated in a culture vessel, the method comprising: adjusting a concentration of cells in the culture vessel to a value of from $3 \times 10^7$ cells/ml to $3 \times 10^8$ cells/ml; in a case in which an average diameter of single cells in the culture vessel is designated as A, adjusting a number proportion of cells having a single cell diameter of $1.4 \times A$ or larger in the culture vessel to 5% or less, and adjusting the number proportion of cells having a single cell diameter in the range of $A \pm A/7$ in the culture vessel to 50% or more.

Cells having a single cell diameter of $1.4 \times A$ or larger may be selectively reduced by applying an external force to the cells accommodated in the culture vessel. It is preferable that a standard deviation of the single cell diameter in the culture vessel is set to A/4 or less.

The method for producing a product according to the disclosed technology can include a step of performing a separation treatment of separating a cell suspension that has been extracted from a culture vessel using a pump, into a cell concentrate having cells concentrated therein and a liquid having a cell concentration that is lower than that of the cell suspension; a step of returning the cell concentrate into the culture vessel; and a step of supplying a fresh medium into the culture vessel. The above-mentioned pump may be a magnetic levitation type pump that rotates a rotating blade suspended in a cell suspension by means of a magnetic force, and cells having a single cell diameter of $1.4 \times A$ or larger may be selectively reduced by applying an external force caused by the liquid flow generated by the pump to the cells.

In a case in which a diameter of the rotating blade of the pump is designated as D meters; a distance between the tip of the rotating blade and an inner wall surrounding a periphery of the rotating blade is designated as L meters; a rotation speed per second of the rotating blade is designated as R; the ratio of a circumference to a diameter of a circle is designated as n; a viscosity of the cell suspension is designated as X pascal-seconds; a liquid feeding pressure of the pump is designated as P pascals; and $Y = X \times D \times \pi \times R/L$, it is preferable that the following relationships are satisfied: $2{,}000 \leq 10{,}000Y + P \leq 80{,}000$, and $3 \log_{10}(P/Y) \leq 5.6$. Y corresponds to the shear stress acting on the cell suspension by the rotation of the rotating blade of the pump. Furthermore, it is preferable that the relationship: $0.1 \leq Y \leq 3$ is satisfied, and it is preferable that the relationship: $500 \leq P \leq 80{,}000$ is satisfied.

In the separation treatment, cells and products can be separated by a known method. For example, the separation treatment may be a membrane separation treatment using a hollow fiber membrane, and the hollow fiber membrane may be a microfiltration membrane. The membrane separation treatment may be carried out by a tangential flow filtration method.

The method for producing a product according to the specified technology can include a collecting step of collecting the liquid that has passed through a hollow fiber membrane. Furthermore, the method can include a step of purifying the liquid collected in the collecting step. The cells accommodated in the culture vessel may be CHO cells, and the product produced from the cells may be an antibody.

According to an embodiment of the invention, the product quality of the product can be increased while the productivity of the product based on high cell concentration culture is maintained.

BRIEF DESCRIPTION OF THE DRAWINGS

Exemplary embodiments according to the technique of the present disclosure will be described in detail based on the following figures, wherein:

FIG. 3 is a table showing the results of carrying out the method for producing an antibody according to an embodiment of the disclosed technology.

DETAILED DESCRIPTION

Figure 1:
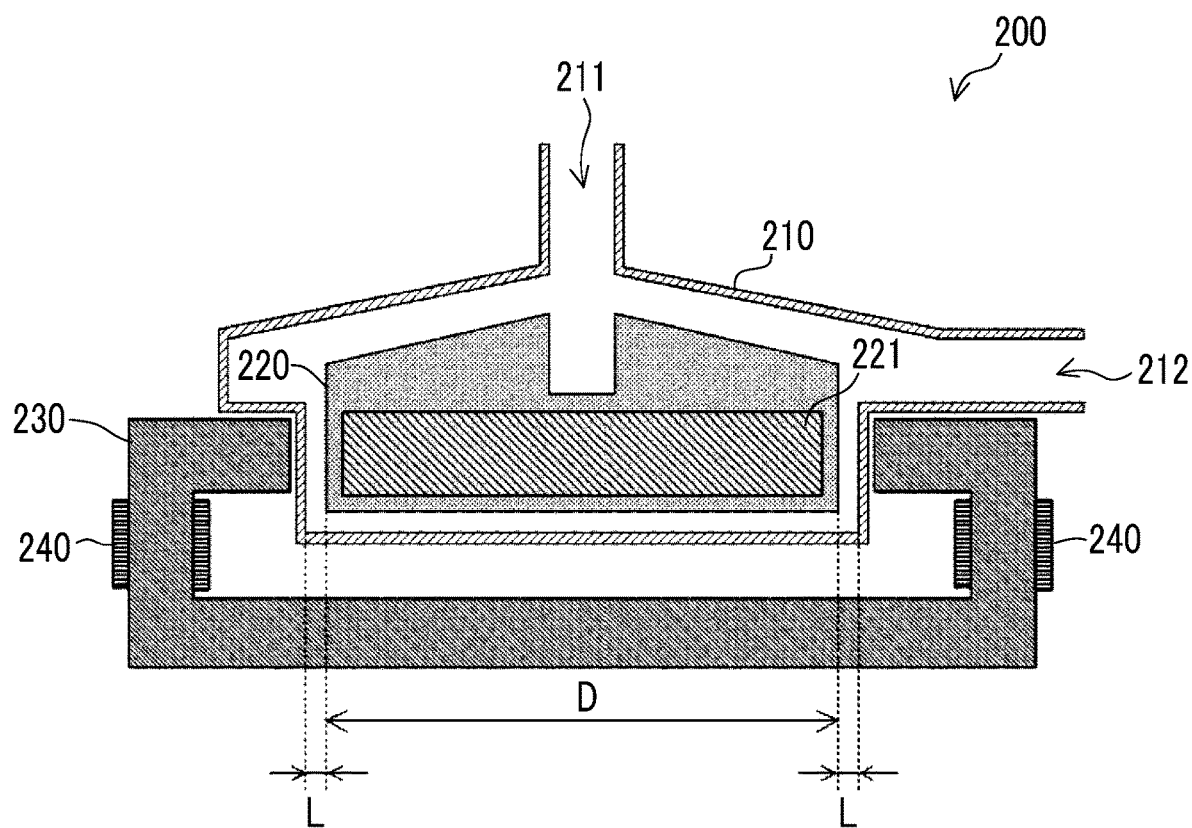
FIG. 1 is a diagram showing an example of the configuration of a magnetic levitation type pump that is applicable to the implementation of a method for producing an antibody according to an embodiment of the disclosed technology.

In regard to the method for producing a product produced by cells according to an embodiment of the disclosed technology, the cells used as the cells that produce a product are not particularly limited; however, examples include eukaryotic cells such as animal cells, plant cells, and yeasts; prokaryotic cells such as *Bacillus subtilis*; and *Escherichia coli*. Animal cells such as CHO cells, BHK-21 cells, and SP2/0-Ag14 cells are preferred, and CHO cells are more preferred. The product produced by cells according to the present disclosure is not particularly limited as long as it is a substance produced by the above-described cells in the culture fluid, and examples include substances such as an alcohol, an enzyme, an antibiotic substance, a recombinant protein, and an antibody. Above all, preferred as the product is a recombinant protein or an antibody, and an antibody is more preferred.

An antibody produced by an animal cell is not particularly limited; however, examples include an anti-IL-6 receptor antibody, an anti-IL-6 antibody, an anti-glypican-3 antibody, an anti-CD3 antibody, an anti-CD20 antibody, an anti-GPIIb/IIIa antibody, an anti-TNF antibody, an anti-CD25 antibody, an anti-EGFR antibody, an anti-Her2/neu antibody, an anti-RSV antibody, an anti-CD33 antibody, an anti-CD52 antibody, an anti-IgE antibody, an anti-CD11a antibody, an anti-VEGF antibody, and an anti-VLA4 antibody. Examples of the antibodies include monoclonal antibodies derived from animals such as human being, mouse, rat, hamster, rabbit, and monkey, as well as artificially modified antibodies such as a chimeric antibody, a humanized antibody, and a bispecific antibody.

The antibody thus obtained or a fragment thereof can be purified until the antibody or the fragment becomes approximately uniform. Separation and purification of the antibody or a fragment thereof may be carried out using conventional separation and purification methods. For example, in a case in which a column for chromatography such as affinity chromatography, a filter, ultrafiltration, salting out, dialysis, SDS polyacrylamide gel electrophoresis, and isoelectric point electrophoresis are selected as appropriate and combined, the antibody can be separated and purified; however, the methods are not limited to these. Measurement of the concentration of the antibody thus obtained can be carried out by measurement of the absorbance, an enzyme-linked immunosorbent assay (ELISA), or the like.

In the method for producing an antibody according to an embodiment of the specified technology, cells are accommodated in a culture vessel together with a medium and are cultured by a perfusion culture method. That is, the method for producing an antibody according to the present embodiment includes a step of performing a separation treatment of separating a cell suspension that has been continuously extracted from a culture vessel using a pump, into a cell concentrate having cells concentrated therein, and a liquid having a lower cell concentration than the cell suspension; a step of returning the cell concentrate thus obtained by the separation treatment to the culture vessel; a step of supplying a fresh medium into the culture vessel; a step of collecting the liquid having a lower cell concentration than the cell suspension, the liquid having been separated by the separation treatment; and a step of purifying an antibody included in the liquid thus collected.

The inventors of the present invention found that in perfusion culture including the respective steps described above, in a case in which the concentration of cells in the culture vessel is maintained in a predetermined range, and at the same time, the number proportion of cells that have grown excessively (hereinafter, referred to as excessively grown cells) in the culture vessel is adjusted to a predetermined value or less, the product quality of an antibody can be increased while the productivity of the antibody based on high concentration culture is maintained by maintaining a high survival ratio for the cultured cells.

Excessively grown cells are aged cells, and they have a lower production capacity for an antibody compared to normal cells and are likely to produce antibodies of low quality. Therefore, by selectively removing excessively grown cells and adjusting the number proportion of excessively grown cells to a predetermined value or less, the quality of the antibody can be increased while a high production capacity for an antibody based on perfusion culture is maintained.

Furthermore, as the concentration of the cells to be accommodated in the culture vessel increases, cell division is inhibited, and excessively grown cells are likely to be produced. Furthermore, a decrease in the viability of cells is brought about. On the other hand, in a case in which the concentration of the cells to be accommodated in the culture vessel is decreased, the productivity of the antibody decreases. Therefore, it is preferable that the concentration of the cells to be accommodated in the culture vessel is controlled to a range in which the productivity of the antibody can be secured while the increase of excessively grown cells and the decrease in the viability of the cells are suppressed, during the culture period.

Specifically, during the culture period, it is preferable that the concentration of cells in the culture vessel is maintained in the range of from $3 \times 10^7$ cells/ml to $3 \times 10^8$ cells/ml, more preferably in the range of from $4 \times 10^7$ cells/ml to $2 \times 10^8$ cells/ml, even more preferably in the range of from $5 \times 10^7$ cells/ml to $1.5 \times 10^8$ cells/ml, and most preferably in the range of from $6 \times 10^7$ cells/ml to $1.2 \times 10^8$ cells/ml.

By adjusting the concentration of cells in the culture vessel to be $3 \times 10^7$ cells/ml or higher, the productivity of the antibody can be secured. Observation of the transition of the cell diameter is made easier. On the other hand, by adjusting the concentration of cells in the culture vessel to be $3 \times 10^8$ cells/ml or less, the decrease in the viability of cells caused by an excessive concentration of the cells and the decrease in the product quality of the antibody produced from the cells can be suppressed. The concentration of the cells in the culture vessel can be adjusted by, for example, a cell bleeding treatment of taking out a portion of cells in a culture vessel 10 at an appropriate timing during the culture period. The concentration of the cells can be obtained by using a known method, for example, an autoanalyzer or can be obtained using an optical microscope.

As described above, it is preferable that excessively grown cells are selectively removed, and the number proportion of excessively grown cells included in the culture vessel is adjusted to a predetermined value or less during the culture period. According to the technology of the present disclosure, in a case in which the average value of the diameter of single cells accommodated in the culture vessel is designated as A, cells having a single cell diameter of $1.4 \times A$ or larger are designated as excessively grown cells.

During the culture period, it is preferable that the number proportion of excessively grown cells having a diameter of 1.4×A or larger in the culture vessel is adjusted to 5% or less, more preferably 4% or less, even more preferably 3% or less, and most preferably from 0.01% to 2.5%. The number proportion of excessively grown cells having a diameter of 1.4×A or larger in the culture vessel being 5% or less implies that removal of the excessively grown cells is appropriately implemented, and thereby the product quality of antibodies can be increased while the production capacity for an antibody is increased thereby. The single cell diameter or the number proportion of excessively grown cells can also be obtained by, for example, using an autoanalyzer or can be obtained by processing an image obtained using an optical microscope.

The average value A of the single cell diameter can be determined by, for example, the following formula.

Average value $A$ of single cell diameter=Sum of cell diameters÷number of cells

The number proportion of excessively grown cells having a diameter of 1.4×A or larger in the culture vessel can be determined by the following formula.

Number proportion (%) of excessively grown cells having a diameter of 1.4×$A$ or larger in the culture vessel=(Number of excessively grown cells having a diameter of 1.4×$A$ or larger)÷(total number of cells)×100

During the culture period, it is preferable that the standard deviation a of the diameters of single cells in the culture vessel is adjusted to be A/4 or less, and more preferably from A/100 to A/5. The standard deviation a of the diameters of single cells in the culture vessel being A/4 or less implies that exclusion of excessively grown cells is being appropriately carried out, and thereby the production capacity for an antibody can be increased, while the product quality of the antibody can be increased at the same time.

Furthermore, during the culture period, it is preferable that the number proportion of cells having a single cell diameter in the range of A±A/7 in the culture vessel is adjusted to 50% or greater, more preferably 55% or greater, and even more preferably from 60% to 95%. In a case in which the number proportion of cells having a single cell diameter in the range of A±A/7 is 50% or greater, it is implied that normal cells are included in a large quantity in the culture vessel, and the homogeneity of cells is high. Thereby, the product quality of the antibody can be stabilized.

The number proportion of cells having a single cell diameter in the range of A±A/7 in the culture vessel can be determined by the following formula.

Number proportion (%) of cells having a single cell diameter in the range of $A±A/7$ in the culture vessel=(Number of cells having a single cell diameter in the range of $A±A/7$)÷(total number of cells)×100

Furthermore, the survival rate of cells in the culture vessel at at least any one time point during the culture period is preferably 90% or higher, more preferably 92% or higher, even more preferably 95% or higher, and most preferably 97% or higher. The survival rate of cells is the number proportion of living cells among all the cells in the culture vessel at a certain time point. By having a survival rate of cells of 90% or higher, the production capacity for an antibody can be increased.

The survival rate of cells can be obtained by a known method, for example, using an autoanalyzer, or can be obtained using an optical microscope.

The separation treatment carried out in the separation step described above may be a membrane separation treatment using a hollow fiber membrane. In this case, a microfiltration membrane (MF membrane) can be used as the hollow fiber membrane. The method for the membrane separation treatment may be a tangential flow method. The tangential flow method is a method of pouring a liquid as an object of the membrane separation treatment so as to cause the liquid to flow along the membrane surface of a filtration membrane and sending small-sized components toward the permeation side. Furthermore, as a separation treatment method other than membrane separation, for example, it is also possible to use a sonic agglomeration method. In the separation treatment for a cell suspension using a sonic agglomeration method, the cell suspension is separated into cells and a supernatant by irradiating the cell suspension with sound waves and thereby agglomerating and settling cells.

Excessively grown cells are vulnerable compare to normal cells. Therefore, as an external force of an adequate magnitude is applied to cells, excessively grown cells can be selectively destroyed and eliminated. Regarding the means for applying an external force to cells, a pump installed in a cell culture apparatus can be used, or an external force can be applied by means of ultrasonic waves. The pump for applying an external force to cells may be, for example, a pump intended for conveying a cell suspension from the culture vessel to the separation treatment unit. Regarding the pump for applying an external force to cells, for example, a magnetic levitation type pump can be suitably used.

Furthermore, these external forces can be exerted on excessively grown cells to loosen the aggregates of cells into single cells, or dead cells can be destroyed and eliminated by the external forces. Thereby, a certain effect of improving the proliferative properties and viability of cells, and the product quality of an antibody is also obtained.

FIG. 1 is a diagram illustrating an example of the configuration of a magnetic levitation type pump 200 that is applicable to the implementation of the method for producing an antibody according to the present embodiment. The pump 200 is configured to include a case 210 having a suction port 211 for suctioning a cell suspension and a discharge port 212 for discharging the cell suspension; a rotating blade 220 accommodated in the case 210; a rotor magnet 221 provided at the bottom of the rotating blade 220; a stator 230 rotating the rotor magnet 221; and a coil 240 wound around the stator 230. By causing an electric current to flow through the coil 240, magnetic force is generated in the stator 230. The rotating blade 220 suspended in the cell suspension inside the case 210 rotates under the effect of the magnetic force generated by the stator 230. As the stator 230 rotates, the cell suspension is suctioned through the suction port 211 and is discharged through the discharge port 212. Since the pump 200 does not have an axis of rotation for driving the rotating blade 220 to rotate, the workload imposed at the time of performing a cleaning treatment and a sterilization treatment can be reduced.

Here, in a case in which the diameter of the rotating blade 220 is designated as D meters (see FIG. 1); the distance between a tip of the rotating blade 220 and the inner wall of the case 210 surrounding the periphery of the rotating blade 220 is designated as L meters (see FIG. 1); the rotation speed per second of the rotating blade 220 is designated as R; the ratio of the circumference to the diameter of a circle is designated as n; and the viscosity of the cell suspension is designated as X pascal-seconds, the shear stress Y exerted on the cell suspension by the rotation of the rotating blade 220 can be roughly estimated by the following Formula (1).

Meanwhile, the rotation speed means the rotation speed set for an apparatus of a rotating blade. The viscosity can be measured based on the method of HS Z 8803, which is a method for measuring the viscosity of a liquid.

$$Y = X \times D \times \pi \times R/L \quad (1)$$

In a case in which the liquid feeding pressure of the pump 200 is designated as P pascals, in the technology of the present disclosure, a value obtained by weighting addition of the shear stress Y and the liquid feeding pressure P is used as an index value F of the external force exerted to the cells by means of a liquid flow generated by the pump 200. The index value F is represented by the following Formula (2).

$$F = 10,000Y + P \quad (2)$$

Weighting of the shear stress Y by 10,000 times is carried out because the influence of the shear stress Y is greater than the influence of the liquid feeding pressure P with regard to selective removal of excessively grown cells. Excessively grown cells are easily destroyable by application of an external force compared to normal cells, and by controlling the index value F represented by Formula (2), excessively grown cells can be destroyed while damage to normal cells is suppressed.

In order to perform selective removal of excessively grown cells, it is preferable that the index value F satisfies the expression: $2,000 \leq F \leq 80,000$, more preferably the expression: $4,000 \leq F \leq 60,000$, even more preferably the expression: $6,000 \leq F \leq 40,000$, and most preferably the expression: $7,000 \leq F \leq 30,000$. In a case in which the index value F is adjusted to 2,000 or more, excessively grown cells can be destroyed efficiently. In a case in which the index value F is adjusted to 80,000 or less, damage to normal cells can be suppressed.

Even in a case in which the index value F is within the range described above, in a case in which the shear stress Y is excessively large, there is a risk that normal cells may be damaged. Furthermore, in a case in which the liquid feeding pressure P of the pump is merely made large, there is a risk that destruction of excessively grown cells may not be promoted. Therefore, it is preferable to control not only the index value F but also the ratio between the shear stress Y and the liquid feeding pressure P. Specifically, it is preferable to satisfy the relationship: $3 \leq \log_{10}(P/Y) \leq 5.6$, and more preferably the relationship: $3.7 \leq \log_{10}(P/Y) \leq 5$. In a case in which the value of $\log_{10}(P/Y)$ is adjusted to 3 or greater, damage to normal cells can be suppressed. In a case in which $\log_{10}(P/Y)$ is adjusted to 5.6 or less, excessively grown cells can be destroyed efficiently.

In order to perform selective removal of excessively grown cells, it is preferable that the shear stress Y satisfies the range: $0.1 \leq Y \leq 3$, more preferably the range: $0.2 \leq Y \leq 2.5$, and even more preferably the range: $0.25 \leq Y \leq 2$. In a case in which the shear stress Y is adjusted to 0.1 or greater, excessively grown cells can be destroyed efficiently. In a case in which the shear stress Y is adjusted to 3 or less, damage to normal cells can be suppressed.

In order to perform selective removal of excessively grown cells, it is preferable that the liquid feeding pressure P satisfies the range: $500 \leq P \leq 80,000$, more preferably $1,500 \leq P \leq 50,000$, and even more preferably the range: $3,000 \leq P \leq 30,000$. In a case in which the liquid feeding pressure P is adjusted to 500 or greater, excessively grown cells can be destroyed efficiently. In a case in which the liquid feeding pressure P is adjusted to 80,000 or less, damage to normal cells can be suppressed.

Figure 2:
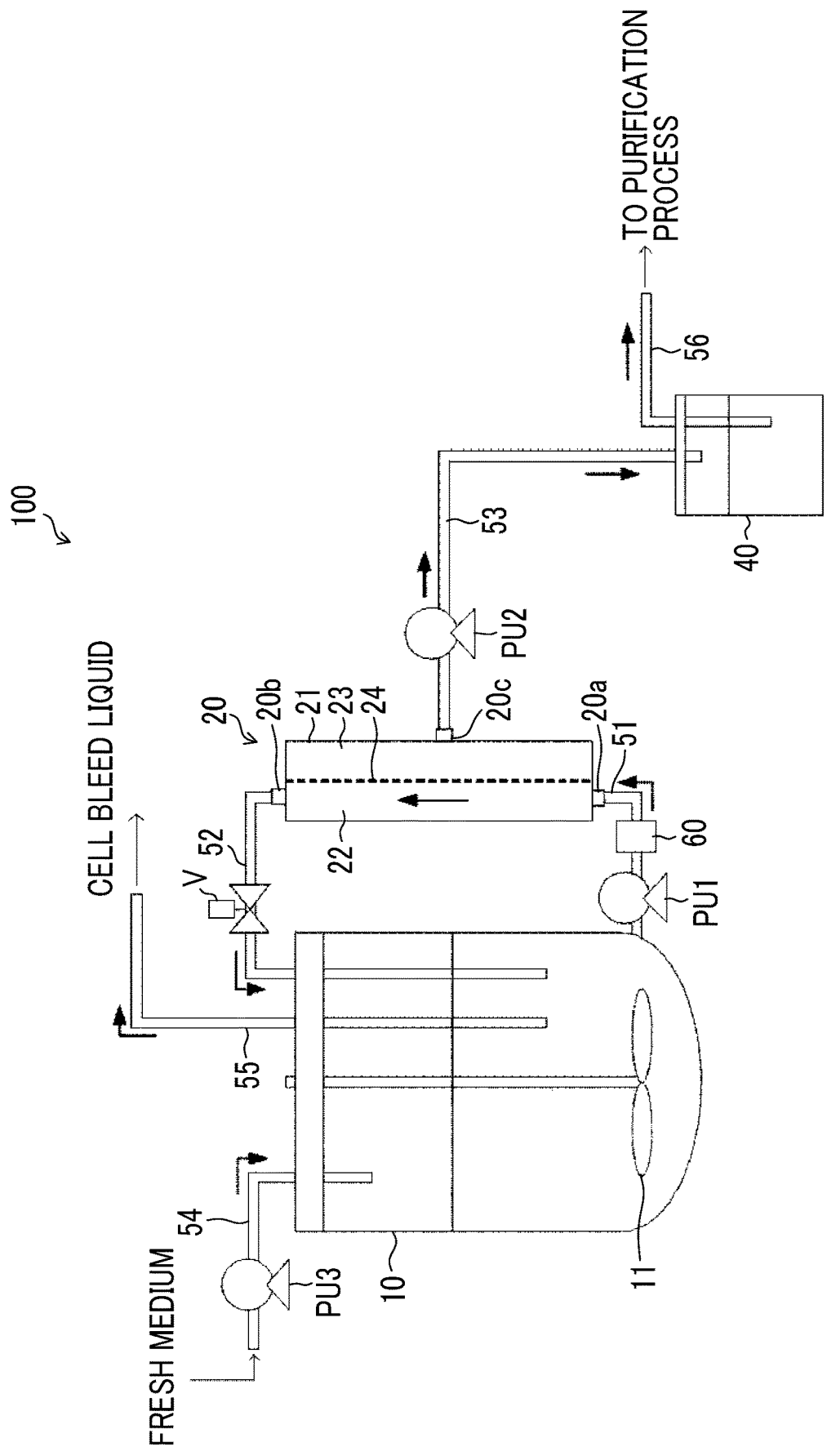
FIG. 2 is a diagram showing an example of the configuration of a cell culture apparatus that is applicable to the implementation of the method for producing an antibody according to an embodiment of the disclosed technology.

FIG. 2 is a diagram illustrating an example of the configuration of a cell culture apparatus 100 that is applicable to the implementation of the method for producing an antibody according to an embodiment of the specified technology.

The cell culture apparatus 100 includes a culture vessel 10 that accommodates cells together with a medium; a filter unit 20 having a filter membrane 24 that applies a membrane separation treatment to a cell suspension extracted from the culture vessel 10; a flow channel 52 that returns the components blocked by the filter membrane 24 to the culture vessel 10; a flow channel 53 that allows the components passed through the filter membrane 24 to pass through; and a collecting tank 40 connected to the flow channel 53.

Inside the culture vessel 10, a stirring apparatus having a stirring blade 11 is provided. As the stirring blade 11 is rotated, the medium accommodated inside the culture vessel 10 is stirred, and homogeneity of the medium is maintained.

The flow channel 51 is such that one end is connected to the bottom of the culture vessel 10, and the other end is connected to an inflow port 20a of the filter unit 20. In the middle of the flow channel 51, a pump PU1 that extracts the cell suspension accommodated in the culture vessel 10 and sends the cell suspension to the filter unit 20 is provided. The pump PU1 is used as a means for applying an external force to cells in order to perform selective removal of excessively grown cells. That is, while a cell suspension is transported from the culture vessel 10 to the filter unit 20, an external force caused by a liquid flow generated by the pump PU1 is exerted to cells, excessively grown cells are selectively destroyed. As the pump PU1, a magnetic levitation type pump 200 illustrated in FIG. 1 can be used. In this case, the shear stress Y applied on the cell suspension can be adjusted by the diameter D of the rotating blade 220, the distance L between a tip of the rotating blade 220 and the inner wall of the case 210 surrounding the periphery of the rotating blade 220, and the rotation speed R per second of the rotating blade 220. The liquid feeding pressure P can be measured using a pressure gauge 60 provided between the pump PU1 and the filter unit 20. The liquid feeding pressure P of the pump PU1 can be adjusted by the degree of opening of a pinch valve V provided on the flow channel 52.

The filter unit 20 includes a vessel 21; and a filter membrane 24 that partitions the space inside the vessel 21 into a supply side 22 and a permeation side 23 and applies a membrane separation treatment to a cell suspension extracted from the culture vessel 10. Furthermore, the filter unit 20 has an inflow port 20a through which the cell suspension flows in; and an outflow port 20b through which the cell suspension flows out, on the supply side 22. The cell suspension extracted from the culture vessel 10 passes through the filter membrane 24 while the cell suspension flows in through the inflow port 20a to the inside of the vessel 21 and flows out through the outflow port 20b to the outside of the vessel 21. The filter unit 20 performs a membrane separation treatment by a tangential flow method of pouring a liquid as an object of the membrane separation treatment so as to cause the liquid to flow along the membrane surface of a filter membrane 24 (in a direction parallel to the membrane surface) and sending small-sized components toward the permeation side 23. The membrane separation treatment based on the tangential flow method may form a flow, in which the cell suspension extracted from the culture vessel 10 circulates in one direction that is parallel to the membrane surface of the filter membrane 24, or may form a flow in which the cell suspension reciprocates along the membrane surface of the filter membrane 24. In a case in which a circulating flow is formed, for example, a KrosFlo perfusion culture flow pass apparatus (KML-100, KPS-200, or KPS-600) of Spectrum Laboratories, Inc., or PuraLev series manufactured by Levitronix GmbH can be suitably used. In a case in which a reciprocating flow is formed, ATF system of REPLIGEN Corporation can be suitably used.

The cells included in the cell suspension do not penetrate through the filter membrane 24, flow out from the outflow port 20b to the outside of the vessel 21, and are returned to the inside of the culture vessel 10 through the flow channel 52. On the other hand, the antibodies included in the cell suspension penetrate through the filter membrane 24 and discharged to the outside of the vessel 21 through the discharge port 20c provided on the permeation side 23. On the permeation side 23, a flow channel 53 provided with a pump PU2 is connected, and the permeation liquid containing the antibodies that have penetrated to the permeation side 23 is collected in the collecting tank 40 through the flow channel 53. The pump PU2 may be a magnetic levitation type pump 200 illustrated in FIG. 1.

A mesh filter composed of a fibrous member woven into a network form can be used as the filter membrane 24. By using a mesh filter, discharge of components that are unnecessary for cell culture, including dead bodies of cells and debris of cells, to the permeation side can be promoted, compared to the case of using a hollow fiber membrane. Thereby, components that are unnecessary for cell culture inside the culture vessel 10 can be effectively removed, and the proliferative properties of cells in the culture vessel 10 can be increased.

Furthermore, a hollow fiber membrane can be used as the filter membrane 24. By using a hollow fiber membrane, a risk that cells penetrate into the permeation side can be reduced, compared to the case of using a mesh filter. Also, a risk that loading caused by cells infiltrating into the filter membrane 24 occurs can be reduced. Thereby, loss of cells can be reduced.

Antibodies included in the permeation liquid that has penetrated through the filter membrane 24 and collected in the collecting tank 40, are sent, through the flow channel 56, to a purification treatment unit (not shown in the diagram) in which purification of antibodies is carried out.

The cell culture apparatus 100 has a flow channel 54 for supplying a fresh medium to the culture vessel 10; and a pump PU3 provided in the middle of the flow channel 54. The pump PU3 may be a magnetic levitation type pump 200 illustrated in FIG. 1.

In order to prevent the concentration of cells in the culture vessel 10 from excessively increasing, a cell bleeding treatment of taking out a portion of cells inside the culture vessel 10 at an appropriate timing during the culture period is carried out. During the cell bleeding treatment, the cells in the culture vessel 10 are discharged to the outside of the culture vessel 10 through a flow channel 55.

The cell culture apparatus 100 illustrated in FIG. 2 performs a separation treatment by means of a membrane separation treatment using the filter unit 20; however, it is also possible to replace the filter unit 20 with a treatment unit of performing a separation treatment according to a sonic agglomeration method.

Examples

An experiment of producing an antibody was performed by performing cell culture by a perfusion culture system under a plurality of conditions that are different from one another, using the cell culture apparatus 100 illustrated in FIG. 2. The contents of the various conditions, evaluation results related to the survival rates of cells varying according to the various conditions, and evaluation results related to the product quality of antibodies thus obtained, are presented in FIG. 3. In Example 13, a separation treatment according to a sonic agglomeration method was carried out instead of a membrane separation treatment using a filter unit 20.

<Experimental Method>

10 L of a fresh medium was introduced into the culture vessel 10, and conditioning was carried out for one day at 37° C.

Cells were seeded such that the cell concentration in the culture vessel 10 would be $1.0 \times 10^6$ cells/ml. CHO cells were used in Examples 1 to 15 and Comparative Examples 1 to 5.

The pump PU1 was driven under predetermined conditions, and a cell suspension was sent to a separation treatment unit (filter unit 20 or a separation treatment unit based on sonic agglomeration). A permeate or a supernatant obtained by a separation treatment was continuously taken out at a rate of 15 L/day, and at the same time, a fresh medium was continuously supplied so that the liquid amount inside the culture vessel 10 would be maintained at 10 L.

Culture was continued until the concentration of cells in the culture vessel 10 reached a predetermined value, and then the cell suspension was continuously taken out from the culture vessel 10 such that the cell concentration would maintain a predetermined value.

On the $10^{th}$ day after the concentration of cells in the culture vessel 10 had reached a predetermined value, samples were obtained from the cell suspension in the culture vessel 10 and a permeation liquid or supernatant obtained by a separation treatment, and evaluations for the survival rate of cells and the product quality of an antibody were performed.

<Various Conditions>

As the pump PU1 for extracting the cell suspension from the culture vessel 10, a magnetic levitation type pump (Examples 1 to 15 and Comparative Examples 1 to 5) and a diaphragm reciprocating ATF pump (Comparative Example 1) were used. For the magnetic levitation pump, PuraLev i30SU, i100SU, 600SU, and 2000SU manufactured by Levitronix GmbH were used. The rotating blade was processed as appropriate such that the diameter D of the rotating blade and the distance L between a tip of the rotating blade and the inner wall surrounding the periphery of the rotating blade would have the respective values shown in FIG. 3. Pump [1] represents i100SU. Pump [2] represents i100SU with a processed rotating blade. Pump [3] represents i30SU with a processed rotating blade. Pump [4] represents 600SU with a processed rotating blade. Pump [5] represents 2000SU with a processed rotating blade. For the diaphragm reciprocating ATF pump, ATF2 manufactured by Repligen Corporation was used.

The rotation speed R per second of the rotating blade of the magnetic levitation type pump and the liquid feeding pressure P were adjusted so as to have the respective values shown in FIG. 3. The liquid feeding pressure P was adjusted by means of the degree of opening of a pinch valve V. The shear stress Y was calculated using Formula (1).

The separation treatment was carried out by a membrane separation method using a hollow fiber type MF membrane (Examples 1 to 12, 14, and 15, and Comparative Examples 1 to 5) and a sonic agglomeration method (Example 13).

Regarding the hollow fiber type MF membrane, a PES (polyether sulfone) filter S06-P20U-10-S having a pore diameter of 0.2 μm of Spectrum Laboratories, Inc. was used.

Regarding the sonic agglomeration, Biosep Acoustic Perfusion System of Applikon Biotechnology B.V. was used.

<Measurement>

On the 10th day after the concentration of cells in the culture vessel 10 had reached a predetermined value, the cell suspension in the culture vessel 10 was extracted, and the concentration of cells, the survival rate of cells, and the diameter of cells were measured using Cell Viability Analyzer Vi-CELL XR of BECKMAN COULTER, Inc. Regarding the software of Vi-CELL, Vi-CELL XR2.04 was used, and the parameters at the time of measurement were set as follows.

Min diameter: 6 μm
Max diameter: 50 μm
Dilution: In a case in which the cell concentration was $100 \times 10^5$ cells/ml or lower, the sample was not diluted, and measurement was made by setting the Dilution as 1. In a case in which the cell concentration was $100 \times 10^5$ cells/ml or lower, the sample was diluted 10 times, and then measurement was made by setting the Dilution as 10.
Cell brightness: 85%
Cell sharpness: 100
Viable cell spot brightness: 75%
Viable cell spot area: 5%
Minimum circularity: 0
Decluster degree: Medium Regarding the average diameter A of a single cell, the output value of Vi-CELL was used. The standard deviation a of the diameter of a single cell, the number proportion of cells having a single cell diameter of 1.4×A or greater, and the number proportion of cells having a single cell diameter in the range of A±A/7 were calculated from the data of the diameter and the number of cells outputted from Vi-CELL.

Regarding the viscosity of the cell suspension, measurement was made using a tuning fork vibration type viscometer SV-10 of A&D Co., Ltd., in a state in which the cell suspension was maintained at 37° C.

A KrosFlo digital pressure monitor (ACPM-201-01N) of Spectrum Laboratories, Inc. was installed immediately after the discharge port of the pump PU1, and the liquid feeding pressure P of the pump PU1 was measured.

Regarding the product quality of the antibody, a decomposition-agglomeration state of the antibody was evaluated by the following procedure by size exclusion chromatography.

(1) 100 μl of Ab Capcher Extra (Protenova Co., Ltd.) was added to 7 ml of a permeate or supernatant obtained by a separation treatment, and the mixture was left to stand for 30 minutes.

(2) A liquid thus obtained was centrifuged, the supernatant was discarded, and a settled gel was collected.

(3) The gel thus obtained was introduced into Micro Bio-Spin Column 6 (Bio-Rad Laboratories, Inc.) set in a 2-ml microtube, 400 μl of an elution buffer (0.1 M Glycine-HCl (pH 2.8)) was added to the column, and the mixture was centrifuged.

(4) 30 μl of a neutralization buffer (1.0 M Tris-HCl, pH 9.0) was added into the liquid that had passed through the column and accumulated in the tube, and the liquid was neutralized.

(5) The neutralized liquid thus obtained was subjected to buffer exchange with a mixed liquid of 80% of a phosphate buffer saline and 20% of ultrapure water using AMICON ULTRA 30 kDa (Merck & Co., Inc.), and the neutralized liquid was prepared so as to have an antibody concentration of 5 mg/L.

(6) The prepared liquid was subjected to size exclusion chromatography (SEC) using a TSKgel G3000SW column manufactured by Tosoh Corporation to measure the size distribution of the antibodies, and the proportion of a main peak was calculated. As the proportion of the main peak is larger, it is implied that the antibodies included in the supernatant are of superior quality.

<Evaluation>

The evaluation determination criteria related to the survival rate of cells are as follows.

A: The survival rate of cells is 97% or higher.
B: The survival rate of cells is higher than or equal to 95% and lower than 97%.
C: The survival rate of cells is higher than or equal to 92% and lower than 95%.
D: The survival rate of cells is higher than or equal to 90% and lower than 92%.
E: The survival rate of cells is lower than 90%.

The evaluation determination criteria related to the proportion of the main peak obtained by size exclusion chromatography are as follows.

A: The proportion of the main peak is 99% or higher.
B: The proportion of the main peak is higher than or equal to 97% and lower than 99%.
C: The proportion of the main peak is higher than or equal to 95% and lower than 97%.
D: The proportion of the main peak is lower than 95%.

In a case in which the average diameter of single cells in the culture vessel 10 is designated as A, Comparative Examples 1 to 5 are different from Example 1 to Example 15 from the viewpoint that the number proportion of cells having a single cell diameter in the range of A±A/7 is lower than 50%, and the standard deviation a of the diameters of single cells is larger than A/4. In Comparative Example 3 and 5, the evaluation related to the survival rate of cells resulted in decision E (lower than 90%) in both cases. In Comparative Examples 1 to 5, the evaluation related to the proportion of the main peak obtained by size exclusion chromatography resulted in decision D (lower than 95%) in all cases. In regard to Comparative Examples 1 to 5, it is thought that selective removal of excessively grown cells is insufficient, and the product quality of the antibody was deteriorated owing to this insufficient removal.

On the other hand, in Examples 1 to 15, the evaluation related to the survival rate of cells resulted in any one of decision A, decision B, decision C, and decision D, and the evaluation related to the proportion of the main peak obtained by size exclusion chromatography resulted in any one of decision A, decision B, and decision C. In regard to Examples 1 to 15, it is thought that selective removal of excessively grown cells was appropriately carried out, the survival rate of cells was increased thereby, and the product quality of the antibody was enhanced. That is, in Examples 1 to 15, the product quality of the product (antibody) could be increased, while the productivity of the product (antibody) by high-concentration culture of cells was maintained. Particularly, in Example 1 to Example 5 and Example 14 to Example 15, in which the number proportion of cells having a single cell diameter of 1.4×A or greater (that is, excessively grown cells) was adjusted to 2.5% or lower, and the number proportion of cells having a single cell diameter in the range of A±A/7 was adjusted to 60% or higher by performing selective removal of excessively grown cells, the evaluation related to the survival rate of cells and the evaluation related to the proportion of the main peak resulted in decision A in all cases.

The present patent application claims priority from JP2017-171331 filed on Sep. 6, 2017, and JP2017-217395 filed on Nov. 10, 2017, the entire disclosures of which are incorporated herein by reference. Furthermore, all publications, patent applications, and technical standards mentioned in this specification are herein incorporated by reference to the same extent as if each individual publication, patent application, or technical standard was specifically and individually indicated to be incorporated by reference.

What is claimed is:

1. A method for producing a product that is produced by cells accommodated in a culture vessel, the method comprising:
performing a separation treatment of separating a cell suspension extracted from the culture vessel using a pump, into a cell concentrate having cells concentrated therein and a liquid having a cell concentration that is lower than that of the cell suspension;
returning the cell concentrate to the culture vessel; and
supplying a fresh medium into the culture vessel,
wherein the cell concentration in the culture vessel is maintained at a value of from $3\times10^7$ cells/ml to $3\times10^8$ cell/ml,
the pump is a magnetic levitation type pump in which a rotating blade suspended in the cell suspension is rotated by a magnetic force, and
in a case in which a diameter of the rotating blade is designated as D meters: a distance between a tip of the rotating blade and an inner wall surrounding a periphery of the rotating blade is designated as L meters; a rotation speed per second of the rotating blade is designated as R: a ratio of a circumference to a diameter of a circle is designated as π; a viscosity of the cell suspension is designated as X pascal-seconds; a liquid feeding pressure of the pump is designated as P pascals; and a shear stress acting on the cell suspension by rotation of the rotating blade is designated as Y, which is calculated by Y=X×D×π×R/L,
the pump is operated such that following relationships are satisfied:
2,000≤10,000Y+P≤80,000 and
3≤$\log_{10}$(P/Y)≤5.6,
so that the cells are selectively reduced by applying an external force caused by the liquid flow generated by the pump to the cells, to thereby obtain a distribution of cells in the culture vessel such that:
in a case in which an average diameter of single cells in the culture vessel is designated as A, the number proportion of cells having a single cell diameter of 1.4×A or greater is 5% or less; and
the number proportion of cells having a single cell diameter in the range of A±A/7 is 50% or more.

2. The method for producing a product according to claim 1, wherein, by applying an external force caused by the liquid flow generated by the pump to the cells, the cells are selectively reduced so that a standard deviation σ of diameters of single cells in the culture vessel is adjusted to A/4 or less.

3. The method for producing a product according to claim 1, wherein in a case in which a diameter of the rotating blade is designated as D meters; a distance between a tip of the rotating blade and an inner wall surrounding a periphery of the rotating blade is designated as L meters; a rotation speed per second of the rotating blade is designated as R; a ratio of a circumference to a diameter of a circle is designated as π; a viscosity of the cell suspension is designated as X pascal-seconds; and a shear stress acting on the cell suspension by rotation of the rotating blade is designated as Y, which is calculated b Y=X×D×π×R/L,
the pump is operated such that the following relationship is satisfied:
0.1≤Y≤3.

4. The method for producing a product according to claim 1, wherein in a case in which a liquid feeding pressure of the pump is designated as P pascals,
the pump is operated such that the following relationship is satisfied:
500≤P≤80,000.

5. The method for producing a product according to claim 1, wherein the separation treatment is a membrane separation treatment of using a hollow fiber membrane.

6. The method for producing a product according to claim 5, wherein the hollow fiber membrane is a microfiltration membrane.

7. The method for producing a product according to claim 5, wherein the membrane separation treatment is performed by a tangential flow filtration method.

8. The method for producing a product according to claim 5, further comprising a collecting step of collecting a liquid that has passed through the hollow fiber membrane.

9. The method for producing a product according to claim 8, further comprising a step of purifying the liquid collected in the collecting step.

10. The method for producing a product according to claim 1, wherein the cells accommodated in the culture vessel are CHO cells.

11. The method for producing a product according to claim 1, wherein the product is an antibody.

* * * * *